(12) United States Patent
Zia et al.

(10) Patent No.: US 7,678,272 B2
(45) Date of Patent: *Mar. 16, 2010

(54) BIOLOGICAL FLUID FILTRATION SYSTEM AND BIOLOGICAL FLUID FILTER USED THEREIN

(75) Inventors: Majid Zia, White Bear Township, MN (US); Chaouki A. Khamis, Minneapolis, MN (US)

(73) Assignee: Hemerus Medical, LLC, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/646,704

(22) Filed: Dec. 28, 2006

(65) Prior Publication Data

US 2007/0102345 A1 May 10, 2007

Related U.S. Application Data

(60) Continuation of application No. 10/962,908, filed on Oct. 12, 2004, now Pat. No. 7,501,059, which is a division of application No. 10/164,668, filed on Jun. 7, 2002, now Pat. No. 6,802,425, which is a division of application No. 09/688,999, filed on Oct. 16, 2000, now Pat. No. 6,427,847, which is a division of application No. 09/272,203, filed on Mar. 19, 1999, now Pat. No. 6,171,493.

(60) Provisional application No. 60/078,848, filed on Mar. 20, 1998, provisional application No. 60/083,484, filed on Apr. 29, 1998.

(51) Int. Cl.
*B01D 36/00* (2006.01)

(52) U.S. Cl. .................. 210/257.1; 210/188; 210/252; 210/436; 210/472

(58) Field of Classification Search ................ 210/188, 210/252, 257.1, 257.2, 435, 436, 472; 55/467; 95/241; 96/155, 236, 240, 243, 361
See application file for complete search history.

(56) References Cited

U.S. PATENT DOCUMENTS

| 2,247,566 | A | * | 7/1941 | Walton | 137/254 |
| 2,401,012 | A | * | 5/1946 | Ornstein | 137/100 |
| 3,892,236 | A | * | 7/1975 | Djerassi | 604/6.03 |
| 5,126,054 | A | * | 6/1992 | Matkovich | 210/641 |
| 5,302,299 | A | * | 4/1994 | Pascale et al. | 210/767 |
| 5,364,526 | A | * | 11/1994 | Matkovich et al. | 210/206 |

(Continued)

OTHER PUBLICATIONS

Virus Size and shape, Encyclopedia Britannica Article, p. 3 (Sep. 2007).*

*Primary Examiner*—John Kim
(74) *Attorney, Agent, or Firm*—Marshall & Melhorn LLC

(57) ABSTRACT

A biological fluid processing or fluid filtration system is provided having novel open and closed loop processing systems wherein the gases transferred into and out of the system during processing pass through a porous medium in upstream and/or downstream gas inlet or outlet housings or vents in a manner which precludes the fluid being processed or filtered from ever contacting the housings or vents. Each housing or vent is separated from the fluid by a column of gas in its respective transfer line. The upstream gas inlet housing or vent is in communication with the unfiltered biological fluid, and the downstream gas inlet housing or vent is in communication with the filtered biological fluid.

5 Claims, 10 Drawing Sheets

U.S. PATENT DOCUMENTS

| | | | |
|---|---|---|---|
| 5,451,321 A * | 9/1995 | Matkovich | 210/641 |
| 5,545,339 A * | 8/1996 | Bormann et al. | 210/806 |
| 5,601,730 A * | 2/1997 | Page et al. | 210/806 |
| 5,670,060 A * | 9/1997 | Matkovich et al. | 210/767 |
| 5,690,815 A * | 11/1997 | Krasnoff et al. | 210/97 |
| 5,776,338 A * | 7/1998 | Mari | 210/252 |
| 6,171,493 B1 * | 1/2001 | Zia et al. | 210/257.1 |
| 6,427,847 B1 * | 8/2002 | Zia et al. | 210/472 |
| 6,802,425 B2 * | 10/2004 | Zia et al. | 210/472 |

\* cited by examiner

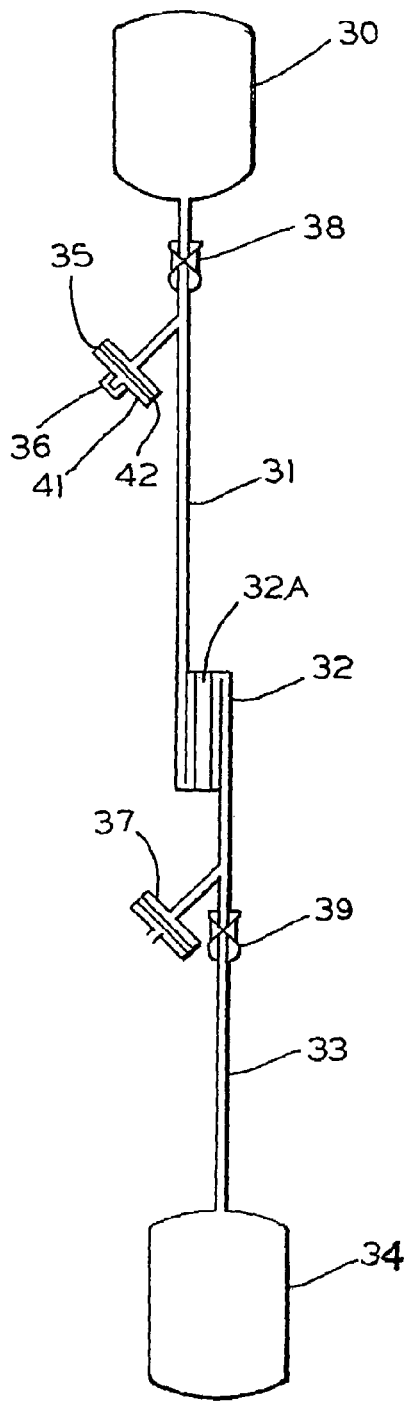
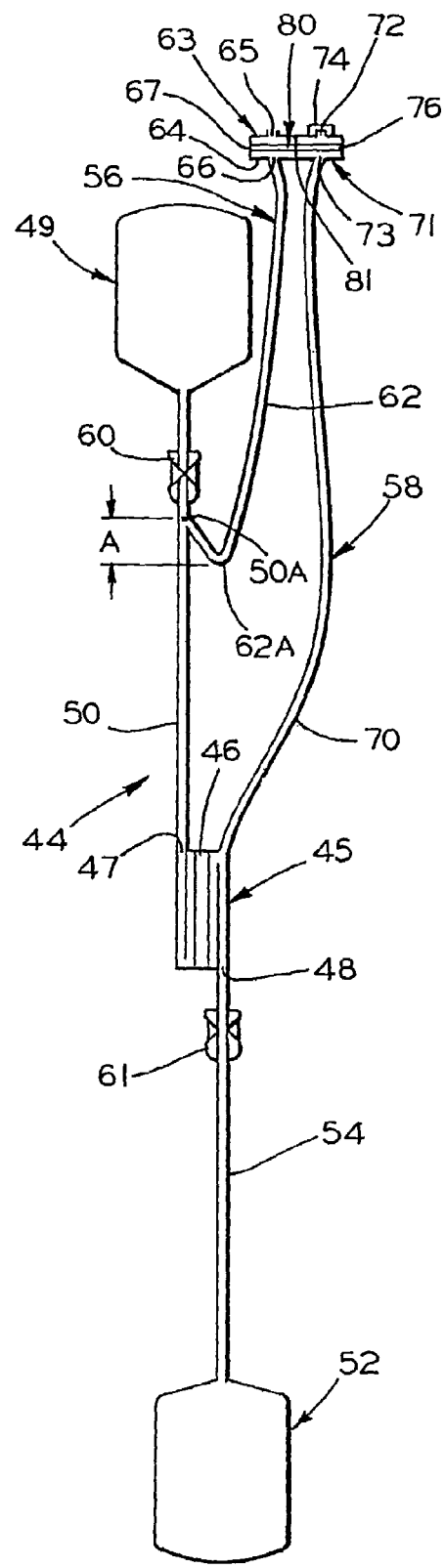
FIG. 1 (PRIOR ART)
FIG. 2

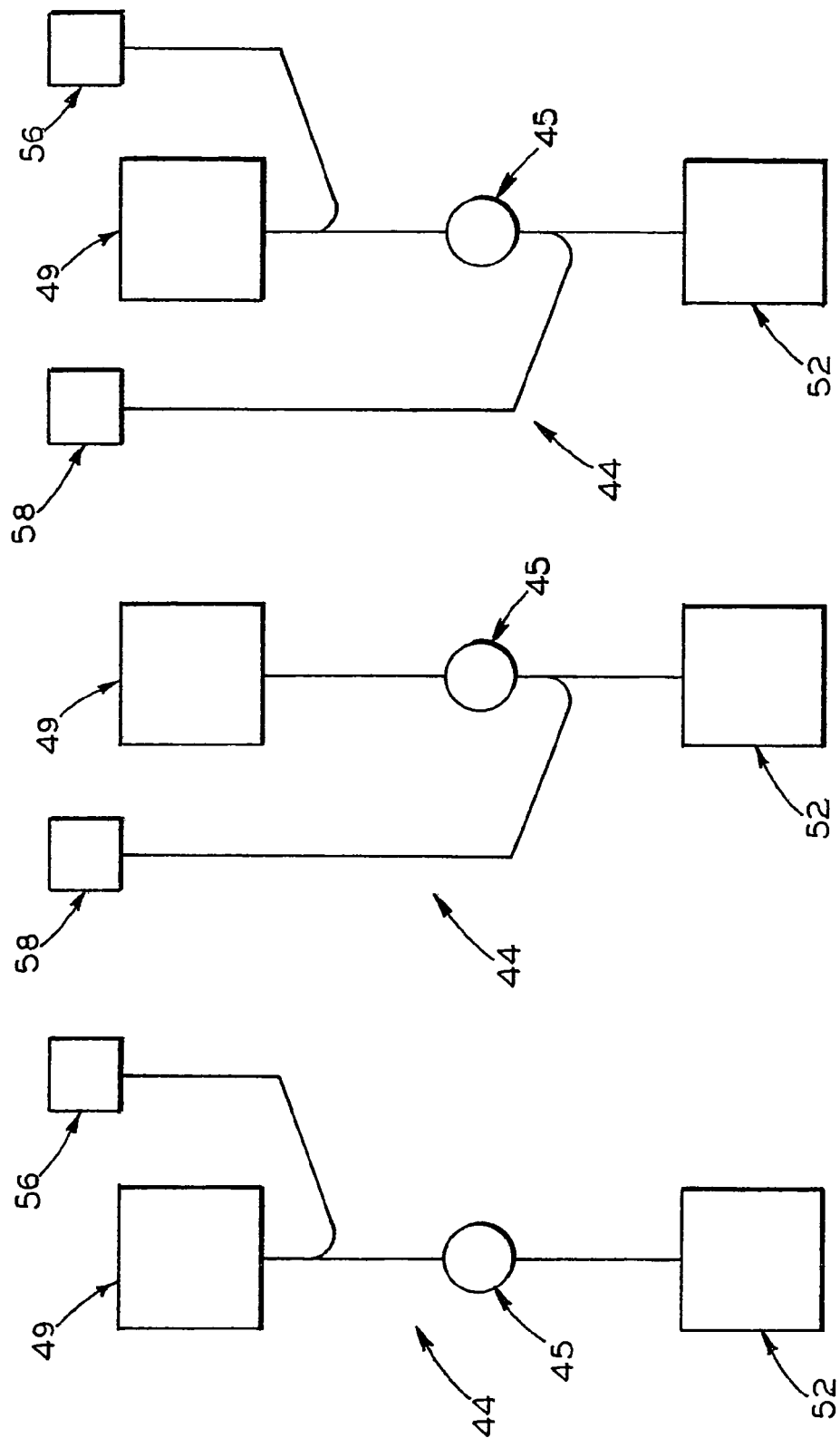

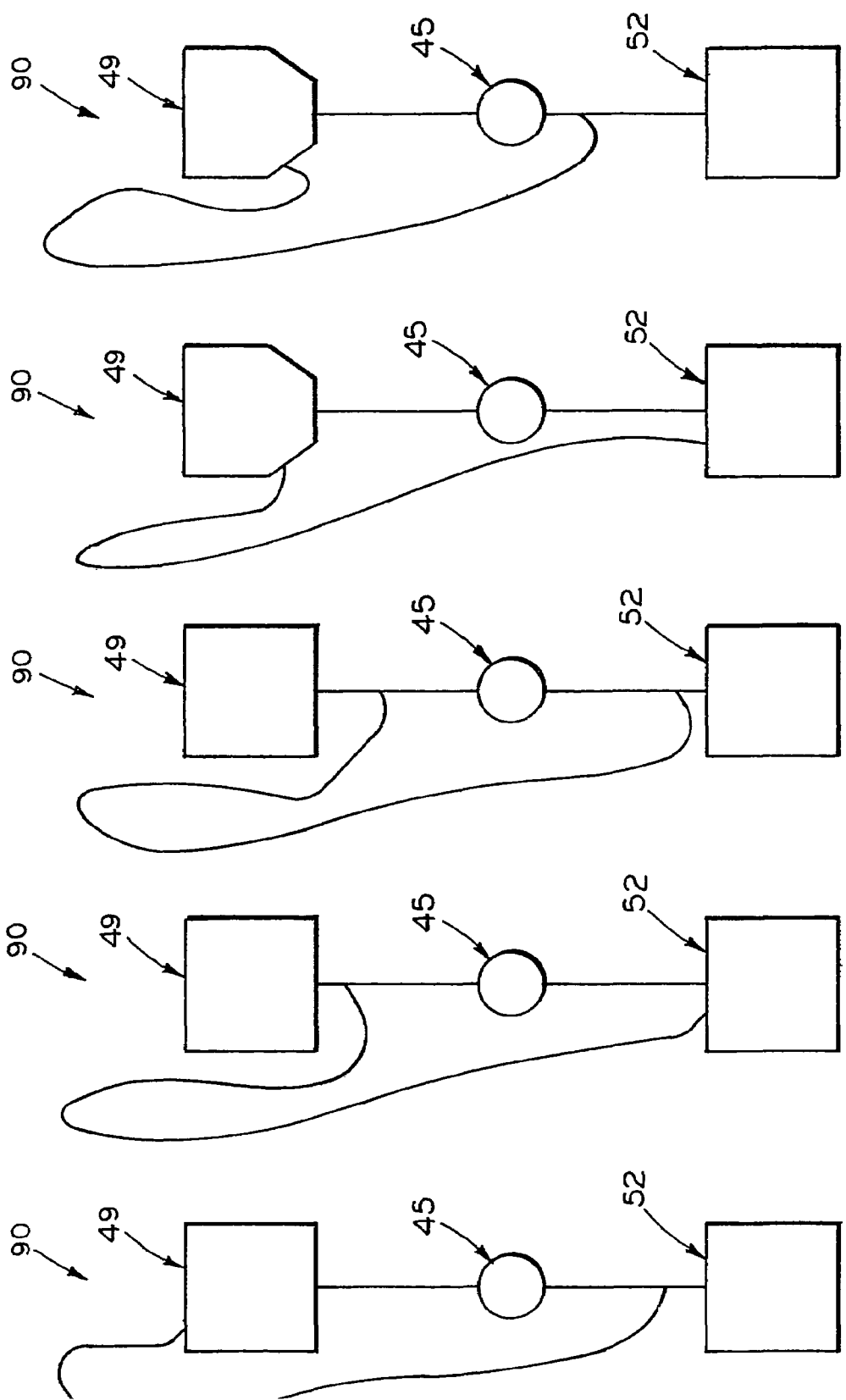

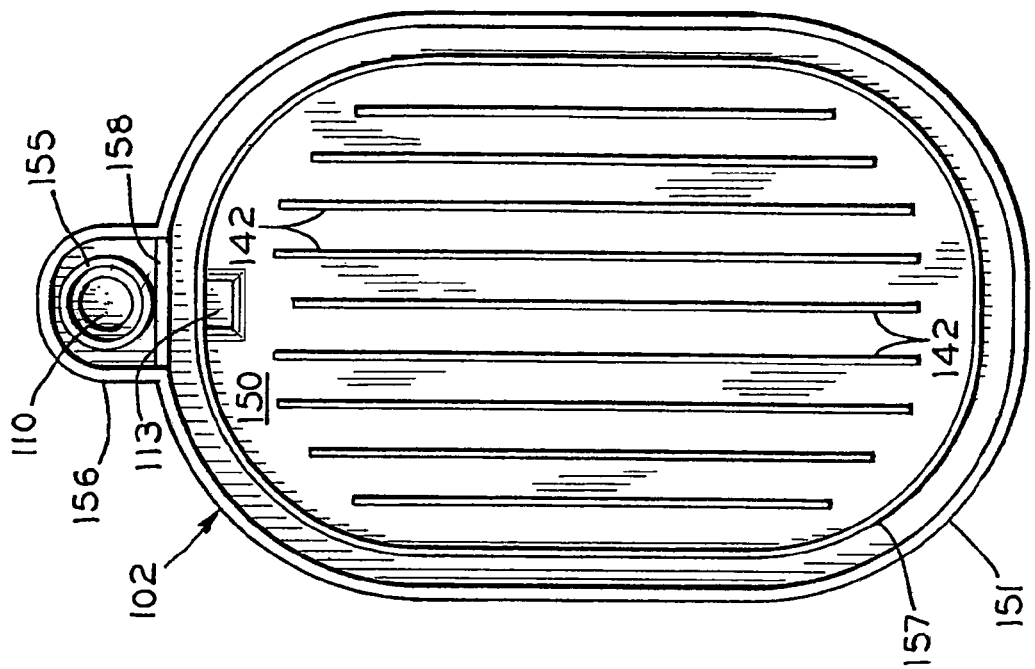
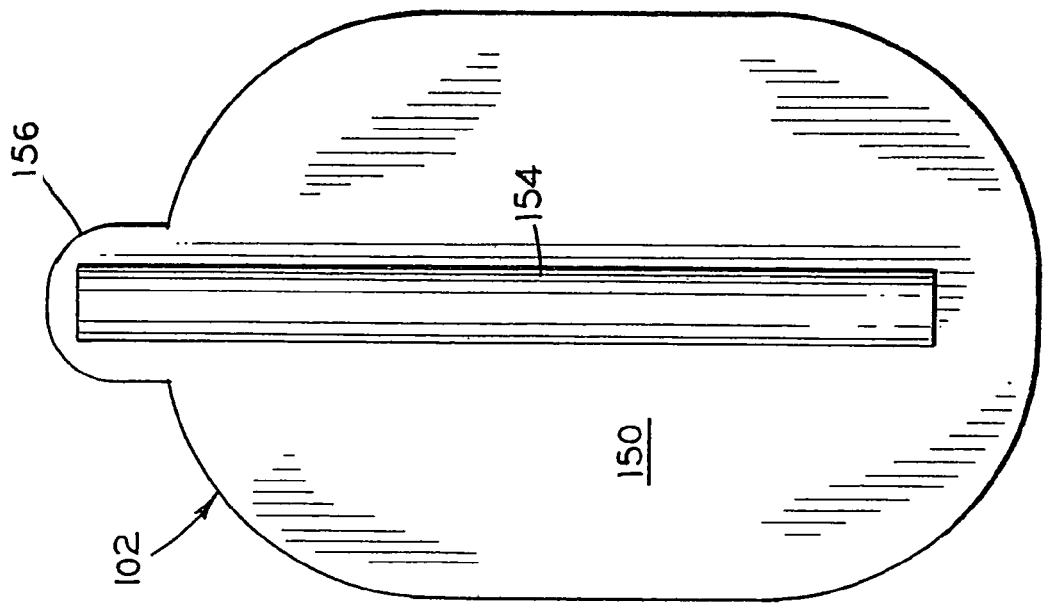

BIOLOGICAL FLUID FILTRATION SYSTEM AND BIOLOGICAL FLUID FILTER USED THEREIN

CROSS REFERENCE TO RELATED APPLICATIONS

This application is a continuation of U.S. application Ser. No. 10/962,908, filed Oct. 12, 2004, now U.S. Pat. No. 7,501,059, which is a divisional application of U.S. application Ser. No. 10/164,688, filed on Jun. 7, 2002, which is now U.S. Pat. No. 6,802,425, which is a divisional application of U.S. application Ser. No. 09/688,999, filed Oct. 16, 2000, which is now U.S. Pat. No. 6,427,847, which is a divisional application of U.S. application Ser. No. 09/272,203, filed Mar. 19, 1999, which is now U.S. Pat. No. 6,171,493. U.S. application Ser. Nos. 10/962,908 and 10/164,668, U.S. Pat. No. 6,427,847, and U.S. Pat. No. 6,171,493 are each hereby incorporated by reference as if set forth in their entirety herein. U.S. application Ser. No. 10/962,908 is pending as of the filing date of the present application.

U.S. application Ser. No. 09/272,203, from which priority is claimed above, claims the benefit, Under 35 U.S.C. 119 (e), of provisional application No. 60/078,848, filed on Mar. 20, 1998, and of provisional application No. 60/083,484, filed on Apr. 29, 1998. The provisional applications 60/078,848 and 60/083,484 are hereby incorporated by reference as if set forth in their entirety herein.

BACKGROUND OF THE INVENTION

1. Field of the Invention

The present invention relates to a method and apparatus for processing biological fluids into their therapeutically valuable components. More particularly, the present invention relates to a method and apparatus for processing donated blood into its therapeutically valuable components. Most particularly, the present invention relates to an improved method and apparatus for processing donated blood into its therapeutically valuable components which uses improved open-loop and closed-loop systems to substantially increase the recovery of all the blood products from the donated blood.

2. Discussion of the Related Art

Methods and apparatus for processing blood are well known in the prior art. U.S. Pat. No. 3,892,236 to Djerassi shows an apparatus for the continuous withdrawal of blood from a human donor, forced extracorporeal circulation of blood of the donor with separation of granulocytes, and return by gravity of the leukocyte-poor whole blood to the donor.

U.S. Pat. No. 5,126,054 to Matkovich shows a venting means for venting gas from the transfer line of a liquid delivery system comprising a housing, a first, liquid-wettable, microporous membrane carried in said housing so as to be in communication with the transfer line, and a second, non-liquid-wettable, gas permeable microporous membrane superimposed on said microporous membrane to the outward side of the housing. Gas in the delivery system is vented from the system so long as the first microporous membrane remains unwetted by the delivery liquid.

U.S. Pat. No. 5,451,321 to Matkovich shows biological fluid processing assemblies having a gas inlet, and/or a gas outlet.

While these devices are generally satisfactory, some of the methods and apparatus of the prior art leave a large amount of biological fluid trapped in various elements of the fluid processing apparatus. While the aforementioned patent U.S. Pat. No. 5,451,321 to Matkovich provides for liquid trapped in various elements of the blood processing system to be recovered either by causing a volume of gas behind the entrapped liquid to push the liquid through those elements and into the designated collection bag, or by pulling the entrapped liquid into the designated collection bag by a pressure differential (e.g. gravity head, pressure cuff, suction and the like), the system still has several drawbacks. One drawback is that they require one or more nonwettable, gas permeable, membranes. This requirement can lead to increased costs over wettable membranes.

Therefore, those skilled in the art continue to search for a method and apparatus to provide for optimal recovery of the biological fluid from biological fluid processing systems, cost reduction and ease of use, and have developed novel open and closed loop systems and methods associated therewith to achieve this goal.

SUMMARY OF THE INVENTION

The problems of the prior art are solved by the present invention utilizing novel open and closed loop biological fluid processing systems which all share the concept that the gases transferred into, out of, or within the biological fluid processing system have the transfer lines arranged or configured in a manner which precludes the biological fluid from ever contacting the upstream and downstream gas inlet or outlet housings or vents, or bypassing the fluid filtration or leukocyte depletion device. Gases are transferred into and out of the biological fluid processing systems through a porous medium in the upstream and downstream gas inlet housings or vents.

Each housing or vent is separated from, and in communication with the biological fluid by a column of gas in the transfer lines. The upstream gas inlet housing or vent is in communication with the unfiltered biological fluid and the downstream inlet or vent is in communication with the filtered biological fluid.

In one embodiment of the present invention, a biological fluid filtration apparatus is provided which includes a fluid filtration or leukocyte depletion device having an inlet and an outlet, a fluid container upstream from and elevated above said fluid filtration or leukocyte depletion device and having an outlet, a first conduit in fluid communication with the outlet of said fluid container and the inlet of said fluid filtration or leukocyte depletion device, a receiving container downstream of said fluid filtration or leukocyte depletion device and having an inlet, a second conduit in fluid communication with the inlet of said receiving container and the outlet of said fluid filtration or leukocyte depletion device, an upstream gas inlet having one of its quadrature ends elevated above said fluid container, and having its other end in fluid communication with said first conduit, and a downstream gas inlet having one of its' end elevated above said fluid container, and having its' other end in fluid communication with said or leukocyte depletion or fluid filtration device.

In another embodiment of the present invention, there is provided a closed loop fluid filtration or leukocyte depletion device including a fluid filtration or leukocyte depletion device having an inlet and an outlet, a fluid container upstream from, and elevated above, said fluid filtration or leukocyte depletion device and having an outlet, a first conduit in communication with the outlet of said fluid container and the inlet of said fluid filtration or leukocyte depletion device, a receiving container downstream of said fluid filtration or leukocyte depletion device and having an inlet, a second conduit in fluid communication with the inlet of said receiving container and the outlet of said fluid depletion device and a bypass line in fluid communication with said fluid container and said receiving container and having a loop portion elevated above said fluid container.

In yet another embodiment of the present invention the upstream gas inlet is eliminated and the downstream gas inlet is connected to the receiving container instead of the fluid filtration or leukocyte depletion device.

In another embodiment of the present invention, the downstream gas inlet may be eliminated.

In still another modification of the present invention, the upstream gas inlet housing or vent and the downstream gas inlet housing or vent may be part of the same inlet device.

Thus, it is an object of the present invention to provide an improved method and apparatus for filtering biological fluids.

It is a further object of the present invention to provide an open gas vent that prevents premature gas introduction into the fluid stream in a biological fluid processing system.

It is a further object of the present invention to provide an open loop biological fluid processing system with transfer lines or conduits arranged or configured in a matter which precludes the biological fluid from contacting the upstream and downstream gas inlet housings or vents, or bypassing the biological fluid depletion device.

Another object of the present invention is to offer a wider choice of materials which may be used in the gas inlet housings or gas outlet housings or vents of biological fluid filtration systems. The present invention does not require wettable membranes. The choice of membranes for the present invention is not limited.

Another object of the present invention is to provide a system of the foregoing nature where gas is transferred into and out of the biological fluid processor through porous medium in the upstream and downstream gas vents.

A still further object of the present invention is to provide an open loop system of the foregoing nature where each gas vent is separated from, and in communication with the biological fluid by a column of gas in the transfer lines or conduits.

A still further object of the present invention is to provide an open loop biological fluid filtration system of the foregoing nature wherein the upstream gas inlet housing or vent, and the downstream gas inlet housing or vent may be a portion of the same inlet device.

A still further object of the present invention is to provide a closed loop biological fluid filtration system having a bypass line bypassing the biological fluid filtration device, the bypass line is arranged such that a column of gas separates the unfiltered biological fluid upstream of the filtration device from the filtered biological fluid downstream of the biological fluid filtration device.

A further object of the present invention is to provide an open loop biological fluid filtration system having an upstream gas inlet elevated above the level of the biological fluid container and having a satellite bag connected to the biological receiving fluid container.

Further objects and advantages of the present invention will be apparent from the following description and appended claims, reference being made to the accompanying drawings forming a part of the specification, wherein like reference characters designate corresponding parts in the several views.

BRIEF DESCRIPTION OF THE DRAWINGS

FIG. 1 is an elevational view of a prior art biological fluid filtration system;

FIG. 2 is an elevational view of a construction embodying the present invention;

FIG. 3 is an elevational view showing a modification of the construction shown in FIG. 2;

FIG. 4 is an elevational view of a further modification of the construction shown in FIG. 2;

FIG. 5 is an elevational view showing a further modification of the construction shown in FIG. 2;

FIG. 7 is an elevational view showing a modification of the construction shown in FIG. 6;

FIG. 8 is an elevational view of a further modification of the construction shown in FIG. 6;

FIG. 9 is an elevational view showing a further modification of the construction shown in FIG. 6;

FIG. 10 is an elevational view showing a further modification of the construction shown in FIG. 6;

FIG. 11 is an elevational view showing a further modification of the construction shown in FIG. 6;

FIG. 20 is a front elevational view of the outlet portion of the construction shown in FIG. 13;

FIG. 21 is a rear elevational view of the construction shown in FIG. 20;

DESCRIPTION OF THE PREFERRED EMBODIMENT

Figure 6:
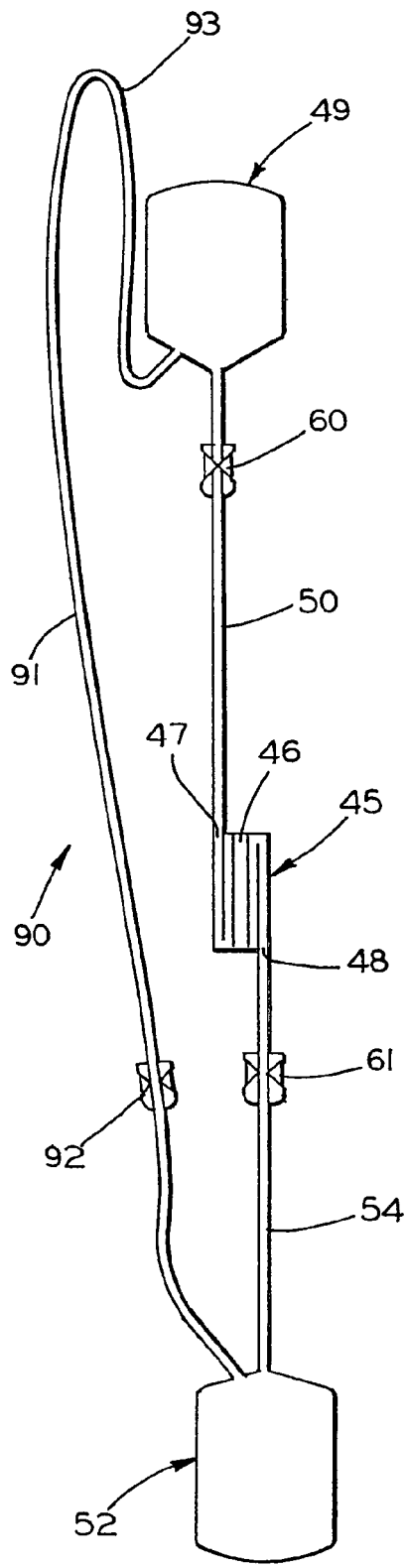
FIG. 6 is an elevational view of a closed loop construction embodying the present invention.

The aforementioned U.S. Pat. No. 5,451,321 to Matkovich shows a biological fluid processing assembly for filter biological processes such as blood. An example of the Matkovich apparatus is illustrated in FIG. 1. The apparatus has a blood collection bag 30 connected by a first conduit 31 to a leukocyte depletion device 32. The leukocyte depletion device 32 is connected by a second conduit 33 to a blood receiving bag 34. A gas inlet 35 having a cover or cap 36, is provided in fluid communication with the first conduit 31 downstream of said collection bag 30, and a gas outlet 37 is provided in second conduit 33 downstream of the leukocyte depletion device 32.

In one embodiment of the prior art, a first clamp 38 is placed on first conduit 31 downstream of the blood collection bag 30 and upstream of the gas inlet 35, and a second clamp 39 is placed on the second conduit 33 downstream of the gas outlet 37. In a typical operation the blood collection bag 30 is sterile and is connected to the conduit 31 as illustrated. The gas inlet 35 is comprised of a housing 41 and a porous medium barrier 42 in addition to cover or cap 36. Additional details of the barrier 42 may be obtained by reference to U.S. Pat. No. 5,451,321.

Prior to the start of blood processing, the inlet clamp 38, the outlet clamp 39, and the gas inlet 35 are all closed. The blood processing is initiated by opening the inlet clamp 38, and allowing the blood to drain from the blood collection bag 30. A column of blood flows through the first conduit 31 into the leukocyte depletion device 32 displacing any gas within the blood processing system. No blood enters the gas inlet device 35 since the gas inlet is closed. The displaced gas is expelled from the system through the gas outlet 37 since the second clamp 39 is closed. As substantially all the gas is expelled from the first conduit 31 and the portion of the second conduit 33 leading to the gas outlet 37, the porous medium is wetted by the blood, and the blood flow seizes or stops at the liquiphobic bearer in the gas outlet 37.

Once the gas outlet 37 is wetted, the second or outlet clamp 39 is opened, and filtered blood flows into the blood receiving bag 34. The gas outlet 37 need not be closed prior to opening of the outlet clamp since the gas outlet is sealed by the wetted porous medium. Blood flows from the collapsible blood container or bag 30 through the leukocyte depletion device 32 and into the blood receiving bag 34 until equilibrium is reached within the system and blood ceases to flow. At this point, all of the blood has not been processed through the leukocyte depletion device 32. The first conduit 31, the filter device 32, and the second conduit 33 are filled with blood.

Removing the cover or cap 36 from the gas inlet 35 allows gas to enter the processing system and drive the blood through the leukocyte depletion device 32. However, since the filter medium 32A within the leukocyte depletion device 32 is wetted, the flow of blood seizes when gas fills the upstream chamber of the filter. When the blood flow seizes, the second or outlet clamp 39 is closed.

It can be seen that, at this point, the downstream side of the leukocyte depletion device 32, and the entire second conduit 33 are filled with blood. With ever increasing need for blood and blood products, those skilled in the prior art have strived to increase the recovery of blood, and such a relatively large quantity of blood being left in the device of the prior art is no longer satisfactory.

In order to solve the recovery problems present in the prior art devices, the open-loop construction shown in FIG. 2 has been developed. There is shown a biological fluid filtration system 44 having a leukocyte depletion device 45 with a filter medium 46, an inlet 47, and an outlet 48. The leukocyte depletion device may be such as the biological fluid filter shown in provisional application Ser. No. 60/083,484, which has been incorporated herein by reference, or any other suitable fluid filtration or leukocyte depletion device.

A blood container 49 is provided upstream from, and elevated above said leukocyte depletion device 45. Blood container 49 is connected to, or in fluid communication with, said leukocyte depletion device 45 through first conduit 50.

There is also provided a blood receiving container 52 downstream of said leukocyte depletion device 45. Leukocyte depletion device 45 is connected to blood receiving container 52 through second conduit 54. An upstream gas inlet 56 is provided in fluid communication with said first conduit 50, and a downstream gas inlet 58 is provided in fluid communication with said leukocyte depletion device 45, downstream of said filter medium 46.

An inlet clamp 60 and an outlet clamp 61 may be provided. It should be understood that one or more of inlet clamp 60 and/or outlet clamp 61 may be provided, and be well within the scope of the present invention.

Upstream gas inlet 56 may take the form of a vent line 62 being connected to an upstream gas inlet housing 64. Vent line 62 may have a U-shaped portion 62A to prevent drawing of gas into biological fluid filtration system 44 until substantially all of the biological fluid has drained from the biological fluid container 49. The other end of vent line 62 should be at a sufficient height such that it is always positioned above the level of the fluid in the biological fluid container 49.

Upstream gas inlet housing or vent 64 has an inlet 65 and an outlet 66. Interposed between the inlet 65 and the outlet 66 in a sealing relationship is at least one layer of a porous medium 67. The porous medium may be such as a bacterial retention medium, a viral retention medium, or other suitable medium.

In a similar manner, the downstream gas inlet 58 may comprise a second vent line 70 connected to a downstream gas inlet housing or vent 71 having an inlet 72 and an outlet 73. A cap or other closure 74 may be used in connection with the opening and the closing of inlet 72. Interposed in the housing 71, between the inlet 72 and the outlet 73 is a second porous medium 76. The second porous medium 76 may also be such as a bacterial retention medium, a viral retention medium, or other suitable medium.

As illustrated, upstream gas inlet housing 64 and downstream gas inlet housing 71 may be provided in a single novel inlet device 80 having a barrier or wall 81 which prevents fluid communication between the upstream gas inlet porous medium 67 and the downstream gas inlet porous medium 76. The upstream medium 67 and the downstream medium 76 may then be formed of a single sheet.

The upstream gas inlet 56 and the downstream gas inlet 58 may be placed in any practicable location as long as they are located such that the blood product being filtered never contacts the porous medium 67. In the preferred embodiment illustrated the porous medium 67 contained within the housing 64 is elevated above the blood container 49, but other locations are well within the scope of the present invention.

In the method of blood processing embodying the present invention, the inlet clamp 60 and the outlet clamp 61 are initially closed. The cap or closure 74 covering the inlet 72 of downstream gas inlet device, housing, or housing portion 71 is also in place.

The blood processing is initiated by opening the inlet clamp 60 and allowing the biological fluid to flow through the first conduit 50. As the fluid flows past the junction 50A, some of the fluid will flow into the upstream gas inlet 56 through vent line 62. A column of liquid of a predetermined, desired, length (shown as dimension A in FIG. 2), between the junction 50A and the bottom of the loop portion of 62A, prevents gas entry into the system until substantially all of the biological fluid has been drained from the biological fluid container 49.

The upstream gas vent may be thought of as a manometer measuring the pressure at the junction 50A. As the level of fluid within the biological fluid container 49 decreases, the pressure at the junction 50A decreases and, therefore, the height of the fluid in the vent line 62 decreases. When substantially all of the biological fluid has drained from the biological fluid container 49, the atmospheric pressure acting on the column of fluid within the vent line 62 will cause all of the fluid within the upstream gas inlet 56 to drain into the conduit 50. The remaining fluid contained with the upstream gas inlet line 62 is drained into the conduit 50 because the upstream gas inlet is open to atmosphere. Thus, dimension A in FIG. 2 must be of sufficient distance such that the above described sequence of events occur. At this point, the leukocyte depletion device 45 downstream of the filter medium 46 and the second conduit 54 between the leukocyte depletion device 45 and the blood receiving container 52, are all filled with filtered biological fluid.

The filtered biological fluid or blood downstream of the filter medium 46 in the leukocyte depletion device 45 may now be recovered by opening the cap or closure 74 covering the inlet 72 of downstream gas inlet device, housing, or housing portion 71. In place of cap 74, a clamp (not shown) could be used on second vent 70.

After this step substantially all of the blood previously unrecovered by the prior art devices is in the blood receiving container 52. Any gas in the receiving container 52 and/or second conduit 54 downstream of the disconnecting point of the blood receiving container 52 may be pushed back up into the second conduit 54 by gently squeezing the blood receiving container 52, and then the outlet clamp 61 can be closed.

As is now evident, the construction shown in FIG. 2 provides an easy method of drainage of substantially all of the biological fluid from the receiving bag 52 through the leukocyte depletion device 45. In addition, the biological fluid filtration system 44 in its preferred embodiment utilizes only a single housing in the inlet device 80, and a single layer of porous medium and substantially all of the filtered biological fluid is recovered. The system has a lower number of parts, is easier to manufacture, and recovers more biological fluid at a lower per unit biological fluid processing cost.

Alternate embodiments of the construction shown in FIG. 2 are illustrated in FIGS. 3-5, with like numerals designating corresponding parts in the several views. Their operation can easily be understood by those skilled in the art in view of the foregoing description.

Figure 12:
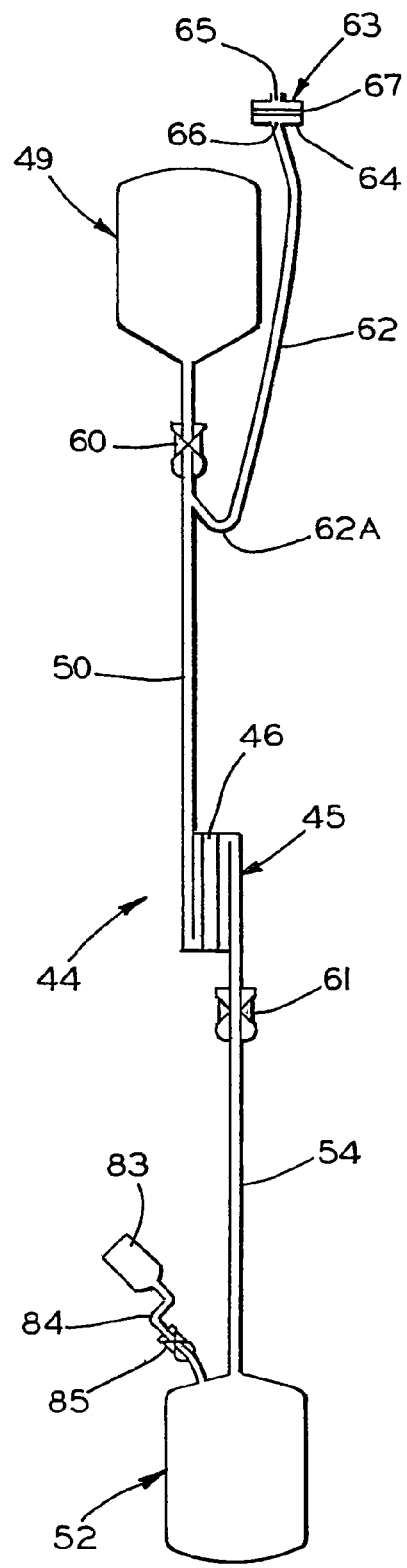
FIG. 12 is an elevational view of a construction embodying the present invention utilizing a satellite bag.
Figure 13:
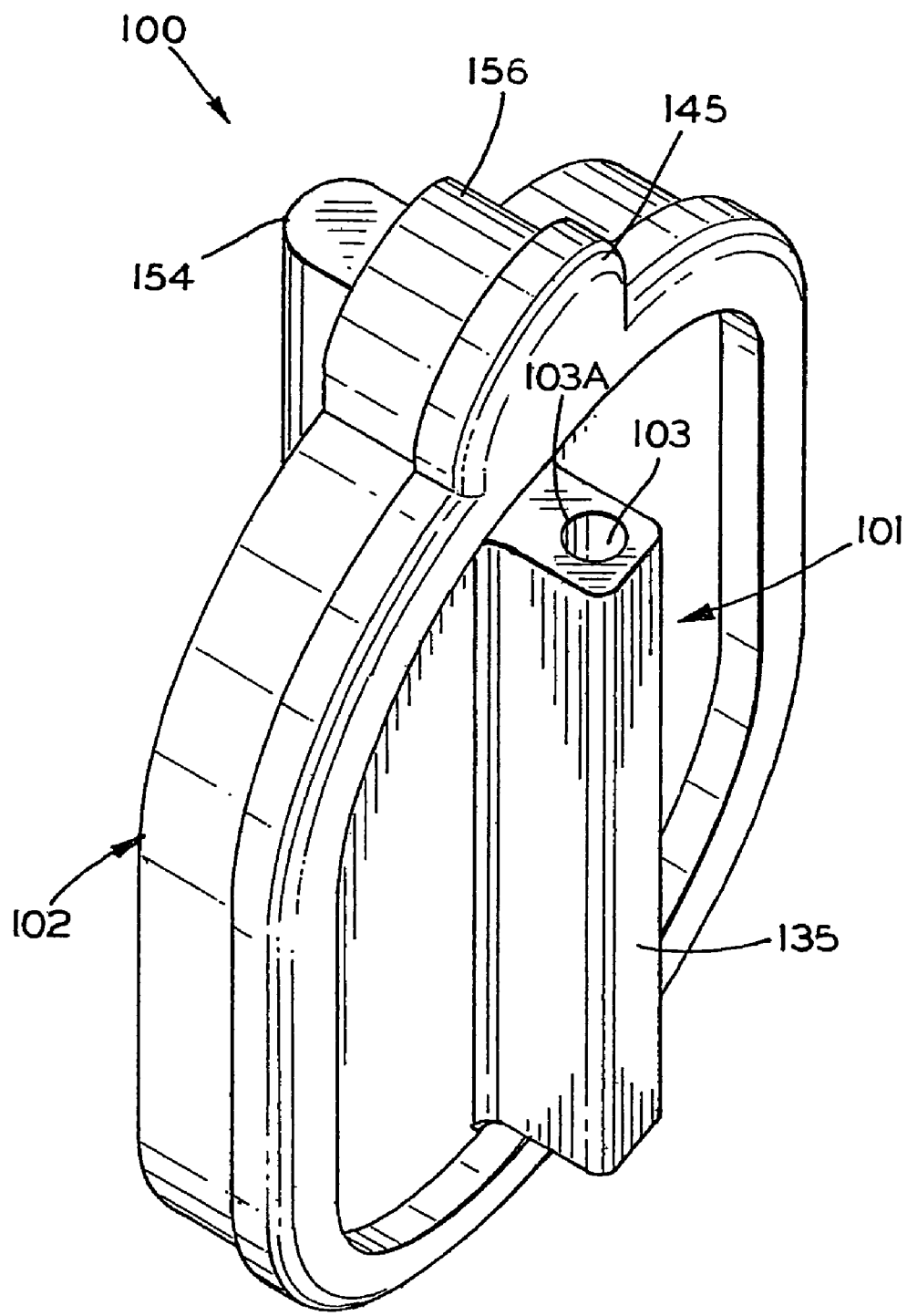
FIG. 13 is a perspective view of a biological fluid filter construction embodying the present invention.

A modification of the present invention utilizing only the upstream gas inlet 56 and a satellite bag 83 is shown in FIG. 12. Satellite bag 83 is connected in fluid communication with blood receiving container 52 by satellite conduit 84. Satellite clamp 85 opens and closes satellite conduit 84. In this embodiment of the present invention, the satellite bag is used to vent the gas displaced from the receiving container 52. The volume of the satellite bag 83 should be sufficient to accept all of the gas displaced. After all the blood has flowed into the receiving container 52; the container is gently squeezed until all of the gas is vented past the satellite clamp 85, at which time the satellite clamp 85 is closed.

Referring now to FIG. 6, there is shown a closed loop biological fluid filtration system 90. As in previous embodiments of the present invention, there is a leukocyte depletion device 45 having a filter medium 46, an inlet 47, and an outlet 48. The filter medium 46 is interposed in a sealing relationship between the inlet 47 and the outlet 48. The system 90 also includes a blood container 49 connected by first conduit 50 to the inlet 47 of leukocyte depletion device 45. Inlet clamp 60 is provided as before.

Provided downstream of the leukocyte depletion device 45 is a blood receiving container 52. A second conduit 54 is connected between the outlet 48 of the leukocyte depletion device 45 and the inlet of the blood receiving container 52. Used in place of the upstream gas inlet 56 and a downstream gas inlet 58 is a by-pass line 91, which may be opened and closed by by-pass clamp 92. A first end of the by-pass line 91 is connected in fluid communication with the blood container 49 proximate the outlet thereof, and the other end of the by-pass line 91 is connected in fluid communication with the blood receiving container 52 proximate the inlet thereof. The loop portion 93 of the by-pass line 91 is positioned such that when the blood container 49 is full of blood, the blood will not reach the loop portion 93 and thus, there can be no flow of blood through the by-pass line. One such position is illustrated in FIG. 6 with the loop portion 93 elevated above the blood container 49.

In place of loop portion 93, a one way check valve or other device may be used such that a column of gas will always separate the unfiltered biological fluid upstream of the filtration device from the filtered biological fluid downstream of the leukocyte depletion device 45. The positioning of the loop portion 93, and the bypass line 91 may also be varied to accomplish this.

The method of operating the closed loop embodiment of the invention differs in several respects from the method used with the open loop embodiment. As illustrated in FIG. 6, the additional by-pass clamp 92 is needed because no gas inlet or gas outlet devices are provided, as were necessary in the prior art. Prior to the start of blood processing, the inlet clamp 60 is closed and the by-pass clamp 92 is open. The blood processing is initiated by opening the inlet clamp 60 and allowing blood to drain from the blood container 49 through first conduit 50 into the leukocyte depletion device 45 and therethrough to the blood receiving container 52. The blood does not by-pass the leukocyte depletion device 45 because of the loop portion 93 of the by-pass line 91 being elevated to a sufficient height. The gas within the closed loop biological fluid filtration system 90 is displaced by the blood flow into the blood receiving container 52. As the blood container 49 approaches its nearly empty condition, the gas stored within the receiving container 52 automatically flows through the by-pass line 91 into the blood container 49 and allows substantially all of the blood to be processed through the leukocyte filtration device 45. It is important to note that the chamber of the leukocyte depletion device 45 downstream of the filter media 46 at this point will be filled with blood, as will the second conduit 54 between the leukocyte depletion device and the blood receiving container 52. If there is any gas left in the receiving container 52 it may be displaced into the by-pass line 91 by closing the outlet clamp 61, gently squeezing the blood receiving container 52 and closing the by-pass clamp 92. In this embodiment of the invention comprising the closed loop biological fluid filtration system, the chamber downstream of the filter medium 46 in the leukocyte depletion device 45 is not drained of blood, nor is second conduct 54. However, the inlet device and the outlet devices of the prior art are eliminated, and a simplified system is provided.

Additional modifications of the closed loop biological fluid filtration system 90 are shown in FIGS. 7-11. Their operation can be understood by those skilled in the art from the foregoing description.

Figures 14, 15:
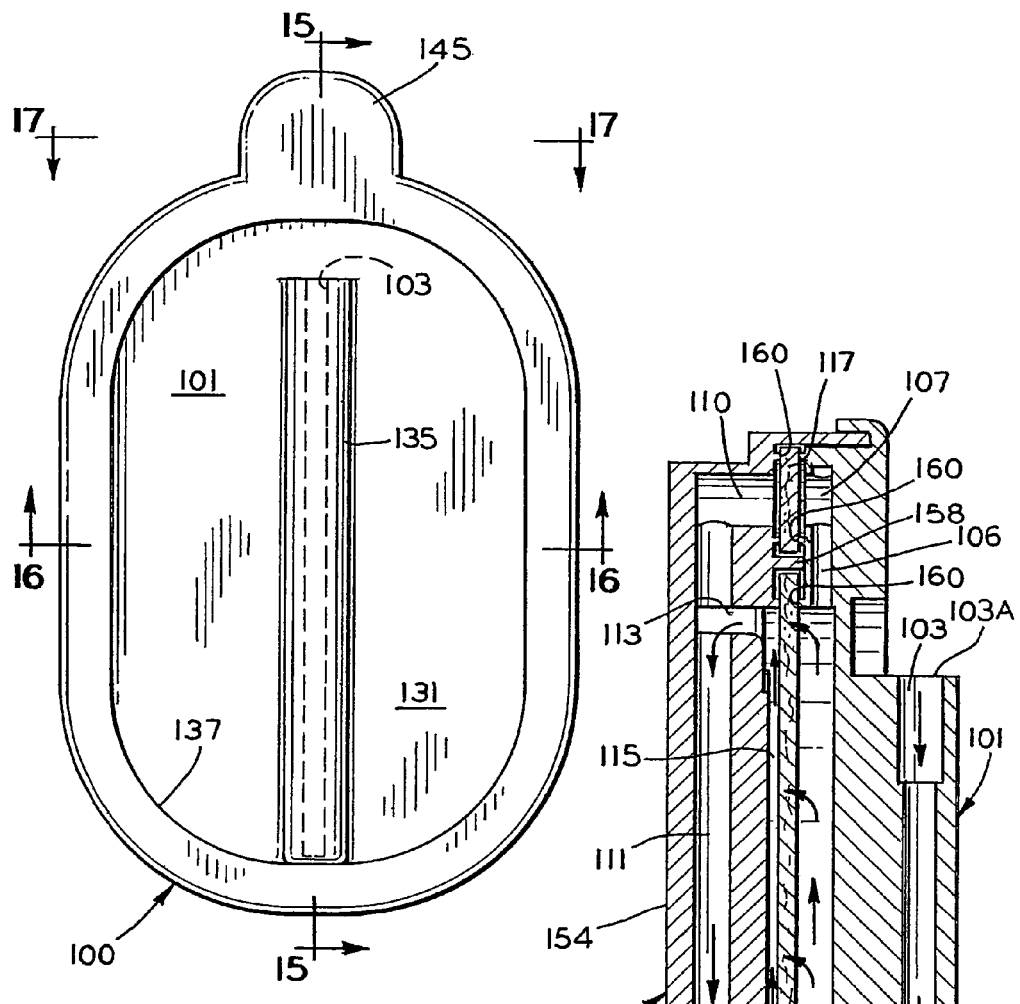
FIG. 14 is a front elevational view of the construction shown in FIG. 13.
FIG. 15 is a sectional view, taken in the direction of the arrows, along the section line 15-15 of FIG. 14.

A more detailed description of the biological fluid filter can be had by referring to FIGS. 13-25. The biological fluid filter 100 consists of an inlet section 101 and an outlet section 102. Referring to FIGS. 14 and 15, the inlet section 101 of biological fluid filter 100 has an inlet 103, including port 103A, communicating with first passage 104, which is in fluid communication with first or inlet chamber 105 through first port of outlet 104A. Further, biological fluid filter 100 has a second passage 106 in fluid communication with both, first or inlet chamber 105, and first vent chamber 107.

The outlet section 102 has a second vent chamber 110 in fluid communication with a third passage 111. Third passage 111 is in fluid communication with outlet 112 through port 112A. A fourth passage 113 is in communication with the third passage 111 and the second or outlet chamber 115. A vent filter element 117 separates the first vent chamber 107 from the second vent chamber 110, and is held in place by means to be described in more detail hereinbelow.

Similarly, a biological filter element 119 separates the first or inlet chamber 105 from the second or outlet chamber 115. Both the vent filter element 117 and the biological filter element 119 may consist of one or more layers, and be made of a wide variety of filter materials. In the embodiment illustrated, they are liquiphilic.

In the preferred embodiment, the vent filter element 117, and the biological fluid filter element 119, are made of the same filter medium, which may be such as glass or nylon fibers. In use, a fluid container (not shown), such as a blood container is placed in fluid communication with inlet port 103A. Similarly, a biological fluid receiving bag (not shown) is placed in fluid communication, by means well known in the art, with outlet port 112A. Fluid flow is initiated and blood flows in the inlet port 103A, through the first passage 104 and through first outlet 104A into inlet chamber 105.

In operation, as the blood enters the inlet chamber 105, the blood may wick into the filter element 119. The blood may wick into the filter element 119 faster, or slower, than the blood level rises in the first or inlet chamber 105. The rate at which the blood wicks into the filter element 119 will depend on the properties of the filter medium being chosen, and the biological fluid being filtered. These properties include the pore size of the medium, the density of the biological fluid, the surface tension of the biological fluid, and the contact angle of the solid-liquid-gas interface. While the blood level is rising in the inlet chamber 105, any air entrapped in chamber 105 is either passing through a portion of the filter element 119 which is not yet wetted, or is proceeding through second passage 106 and being vented out the vent filter element 117.

As the blood level continues to rise in inlet chamber 105, at some point, the biological filter element 119 will be sufficiently "wetted", and the biological fluid being filtered will "breakthrough" the filter element 119, and will start flowing into outlet chamber 115. The fluid breakthrough depends on the pore size of the material, the surface tension and the contact angle, as well as the pressure differential across the filter element 119.

Due to the pressure differential across the biological filter element 119, the biological fluid continues to flow up into second passage 106. If the pressure differential is sufficient, the biological fluid will contact the vent filter element 117, which is the preferred embodiment. If the vent filter element 117 is also made of a liquiphilic media, it will become "wetted out". However, by this time all the gas entrapped in inlet chamber 105 has either passed previously through biological filter element 119 or through vent filter element 117 and accomplished one of the objects of the invention.

Referring now to FIGS. 14-19, the construction of the inlet section 101 of the biological fluid filter 100 may be clearly understood. The biological fluid filter 100 includes an inlet section 101 which is bonded to an outlet section 102 by a seal 130. The seal 130 is preferably an ultrasonic seal. It can be understood by those skilled in the art that other seals such as heat seals, adhesive seals, or any other air tight seal may be used.

Inlet section 101 includes a recessed top wall 131, and down standing side walls 132 extending around the periphery of the recessed top wall 131. A down standing peripheral ridge 133 extends around the periphery of the down standing side wall 132 and forms a part of the mechanism which holds the vent filter element 117 and the biological filter element 119 in place, as will be more fully explained hereinafter. A first protuberance 135 extends from the recessed top wall 131, and carries the inlet 103 and first passage 104 as previously described. First or outlet port 104A which is in fluid communication with the first passage 104 can be seen in FIG. 19. A recess 136, provided by the combination of the top surface of the recessed top wall 131 and the peripheral side walls 137 almost completely surrounds the protuberance 135.

A peripheral flange 138 depends from the peripheral sidewall 137 and forms a groove 139 extending around the periphery of the inlet section 101 of the biological fluid filter 100. The groove 139 forms a portion of the means by which the seal 130 between the inlet section 101 and the outlet section 102 of the biological fluid filter 100 is formed. A plurality of down standing ribs 142 are provided on the lower surface of the recessed top wall 131 for purposes to be described.

The inlet portion 101 of the biological fluid filtration device also has an extended portion 145 which contains second passage 106 (FIG. 15) in fluid communication with first vent chamber 107. The same flange 138 and groove 139 are provided in the extended portion 145 of the inlet section 101 as are provided in the remainder of the inlet section 101, so that the inlet section 101 will properly mate with the outlet section 102 to be described. A circular ridge 147 is provided about the first vent chamber 107 to aid in holding the vent filter, as will be further described.

Referring now to FIGS. 15-17 and 20-21, the construction of the outlet portion 102 of the biological fluid filter 100 will be clearly understood. The shape of the outlet section 102 of the biological fluid filter 100 is complimentary in shape to the inlet section 101 so that the inlet section 101 may act as a closure to the outlet section 102, or vice versa. It can easily be understood by those skilled in the art that the biological fluid filter 100 may be of any desired shape, such as the generally oval shape thus far described, the diamond shape of the modification shown in FIG. 22 or 24, or any other desired shape. Similar to the inlet section 101, the outlet section 102 of the biological fluid filter 100 has a bottom wall 150 and upstanding sidewall 151. The top of the upstanding sidewall 151 fits into the groove 139 in the inlet portion 101, and is preferably sonically welded to form the seal 130. A second protuberance 154 is provided on the exterior portion of the bottom wall 150 and carries the third passage 111, fourth passage 113, and a portion of the vent chamber 110. A second circular ridge 155, complimentary in shape to the circular ridge 147, is provided. The protuberance 154 covers a portion of the extended portion 156 of the outlet portion 102 of the biological fluid filter 100.

Figure 16:
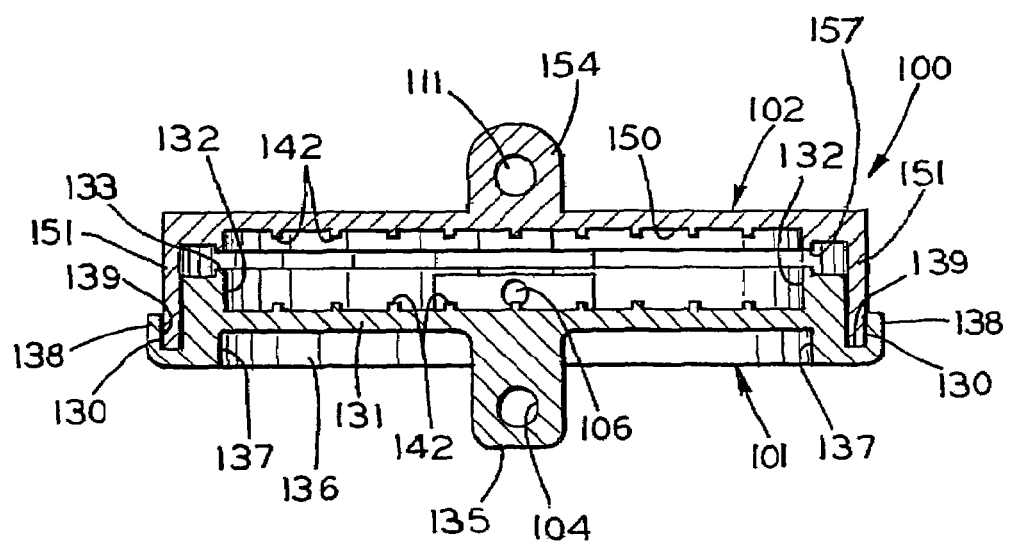
FIG. 16 is a sectional view, taken in the direction of the arrows, along the section line 16-16 of FIG. 14.
Figure 17:
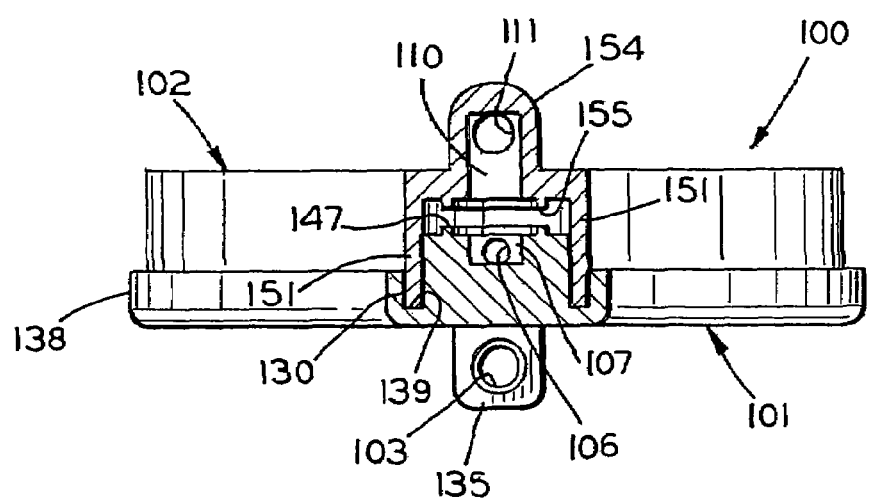
FIG. 17 is a sectional view, taken in the direction of the arrows, along the section line 17-17 of FIG. 14.
Figure 19:
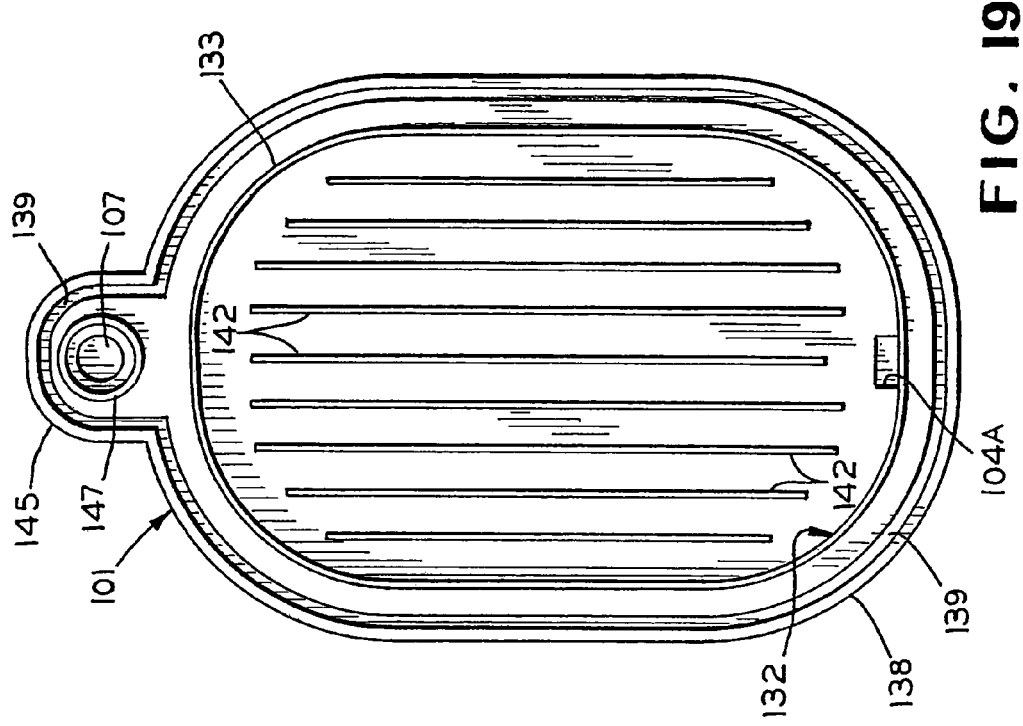
FIG. 19 is a rear elevational view of the construction shown in FIG. 18.
Figure 18:
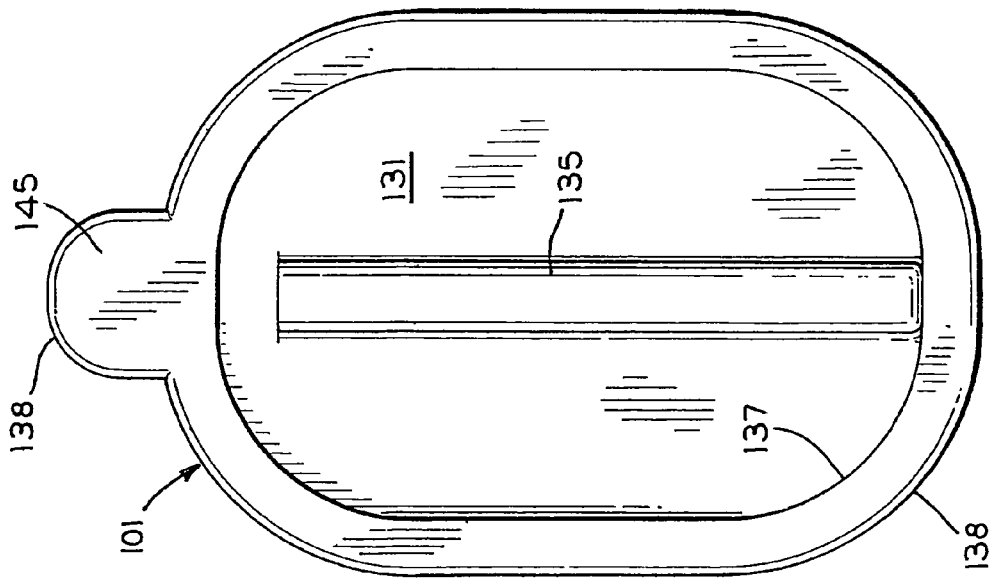
FIG. 18 is a front elevational view of the inlet portion of the construction shown in FIG. 13.

As seen in FIG. 16, a further plurality of ribs 142 is provided on the interior surface of the bottom wall 150 to help support the biological filter element 119 and provide flow in the second or outlet chamber 115 of the biological fluid filter 100. An upstanding ridge 157 is provided in a spaced apart relationship to the upstanding sidewall 151. As with the circular ridges 147 and 155 when the outlet portion 22 and the inlet portion 21 are in mating relationship, the down standing ridge 133 and the upstanding ridge 157 will be in a 180 degree opposed relationship. As can be seen in FIG. 15 these ridges will provide the pinch seals 160 for the vent filter element 117 and the biological filter element 119. An ultrasonic weld ridge 158 is provided to separate vent filter 117 and biological filter element 119, and to provide additional support for the biological fluid filter 100.

Figure 22:
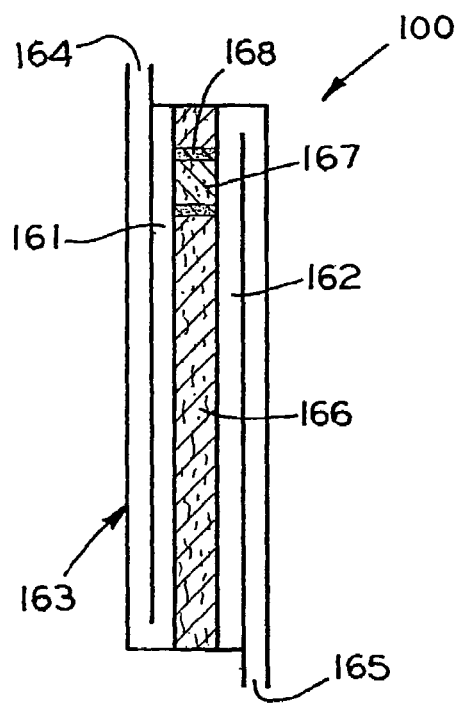
FIG. 22 is a modification of the construction shown in FIG. 13.
Figure 23:
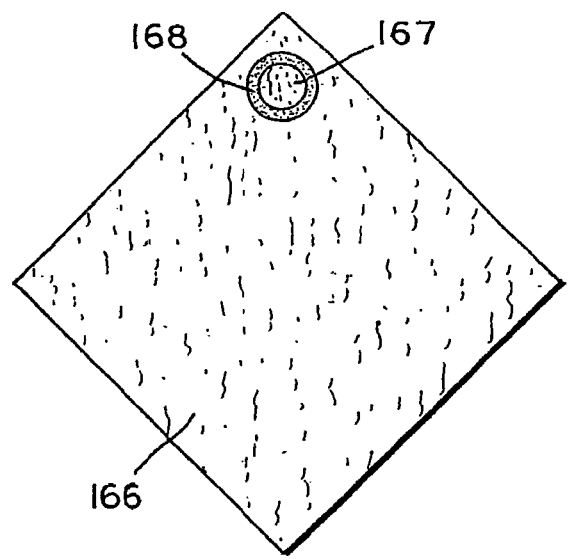
FIG. 23 is a diagrammatic view of the filter medium shown in the construction of FIG. 22.

Referring to FIGS. 22 and 23, there is shown a modification of the biological fluid filter 100 previously described. In this modification of the invention, the biological fluid filter 100 has a housing 163, which may be constructed in a manner similar to that just described, or may be constructed by other means well known in the art. The housing has an inlet 164 to which a biological fluid container of the type well known in the art would be in fluid communication during operation. The housing 163 also has an outlet 165 through which the filtered fluid passes. The outlet 165 would be in fluid communication with a biological receiving container (not shown).

A filter element 166 would be sealingly mounted within the housing between inlet 164 and outlet 165. In this modification of the biological fluid filter 100, instead of there being a separate and distinct vent filter element 117, the vent filter element 167 is embedded in the biological fluid filter element 166 i.e., the filter medium is divided into two or more sections. The biological filter element 166 may be made of a liquiphilic filter medium, and the embedded vent filter element 167 may also be made of a liquiphilic filter medium, surrounded by a solid or liquiphobic barrier 168. In operation, this modification of the biological fluid filter would operate in a similar manner to that just described because of the liquiphilic nature of the biological filter element 166, until the element was completely saturated. As the blood was rising in the inlet chamber 161, any entrapped gas would pass through the embedded vent filter element 167 until the level of the blood surpassed the solid or liquiphobic barrier 168. At this time, virtually all of the entrapped gas would be downstream of the biological filter element 166, the element would be completely saturated, and blood would now freely flow into the outlet chamber 162.

Figure 24:
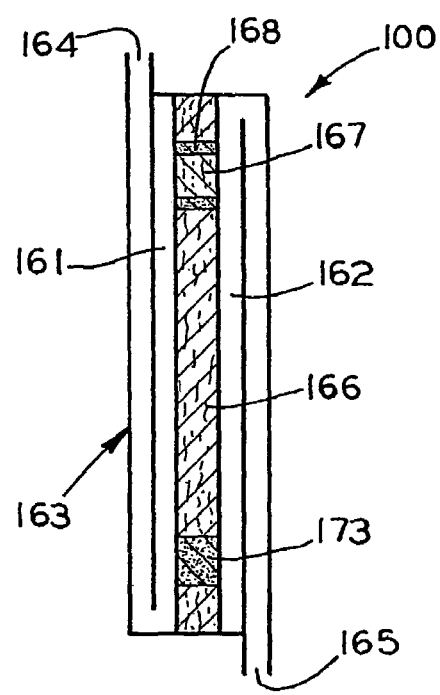
FIG. 24 is a diagrammatic view of a further modification of the construction shown in FIG. 13.
Figure 25:
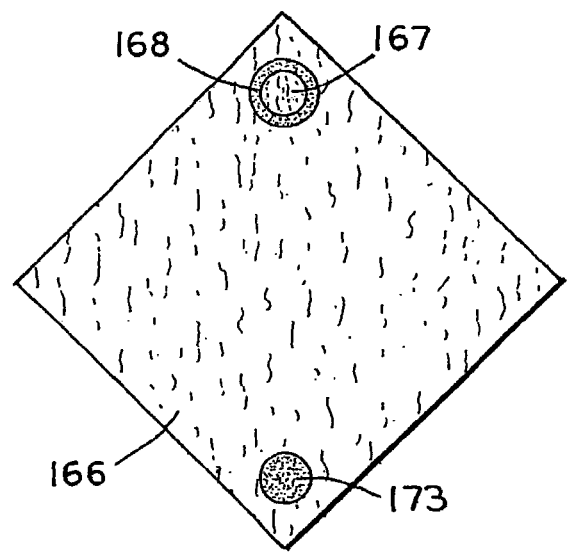
FIG. 25 is a diagrammatic view of the filter medium shown in the construction shown in FIG. 24.

Another modification of the biological fluid filter 100 is shown in FIGS. 24 and 25. As before, there is a filter housing 163 having an inlet 164 communicating with an inlet chamber 161, and an outlet 165 communicating with an outlet chamber 162. In this modification of the invention, the biological filter element 166 has a first embedded liquiphilic gas vent 167 surrounded by a solid barrier 168, and a second embedded liquiphobic gas vent 173 i.e. the filter medium is divided into two or more sections, separated form each other, in this case, three sections.

In operation, a biological fluid container known in the art (not shown) will be in fluid communication with inlet 164. As blood is released from the biological fluid container it will flow into the inlet chamber 161 and come into contact with the bottom of the biological fluid filter element 166. Since filter element 166 may be a liquiphilic porous medium, the blood level may wick up in the liquiphilic porous medium 166 faster than the level in the chamber 161. The blood will not pass through the liquiphobic second embedded gas vent 173. The second embedded gas vent 173 will have no effect on the operation of the biological fluid filter 100 while the liquid level continues to rise in inlet chamber 161. However, the difference between the embodiment of the invention shown in FIGS. 22 and 23, and 24 and 25, becomes apparent when all of the blood has been released from the biological filter container and the level starts dropping in the inlet chamber 161. The vent filter element 167 will stay wetted out as the level in the inlet chamber 161 drops because of the blood present in the outlet chamber 162. However, as the level in the inlet chamber 161 continues to drop it will drop below the level of the liquiphobic second embedded gas vent 173. Since gas vent 173 did not wet out, when the blood level drops, air will pass from the inlet chamber 161 through the second embedded gas vent 173, and aid in draining the filter element 166, as well as the outlet chamber 162, through the outlet 165.

Therefore, by carefully studying the problems present in prior art biological filtration fluid systems; I have developed a novel method and apparatus for biological fluid filtration.

In accordance with the provisions of the patent statutes, the present invention has been described in what is considered to represent its preferred embodiment. However, it should be noted that the invention can be practiced otherwise than as specifically illustrated and described without departing from its spirit or scope.

We claim:

1. A fluid apparatus including: a) a fluid container having an outlet, b) a first conduit in fluid communication with the outlet of said fluid container, c) a vent line in fluid communication with said first conduit and connected directly to the first conduit, and having an outlet at a sufficient height so that a fluid being filtered does not exit out of said vent line, and having a U-shaped portion which prevents gas entry into said fluid apparatus until a desired amount of fluid has exited said fluid container.

2. The fluid apparatus defined in claim 1, and further including an upstream gas inlet housing in fluid communication with said vent line.

3. The fluid apparatus defined in claim 2, wherein said gas inlet housing includes: a) an inlet open to atmosphere, b) an outlet connected to said vent line, and c) at least one layer of a porous medium interposed between said inlet and said outlet.

4. The fluid apparatus defined in claim 3, wherein said at least one layer of a porous medium is a bacterial retention medium.

5. The fluid apparatus defined in claim 3, wherein said at least one layer of a porous medium is a viral retention medium.

\* \* \* \* \*